US009018963B2

(12) United States Patent
Sim et al.

(10) Patent No.: US 9,018,963 B2
(45) Date of Patent: Apr. 28, 2015

(54) ENVIRONMENT SENSOR

(75) Inventors: Dongyoun Sim, Tokyo (JP); Masaru Soeda, Tokyo (JP)

(73) Assignee: Azbil Corporation, Tokyo (JP)

( * ) Notice: Subject to any disclaimer, the term of this patent is extended or adjusted under 35 U.S.C. 154(b) by 305 days.

(21) Appl. No.: 13/607,459

(22) Filed: Sep. 7, 2012

(65) Prior Publication Data

US 2013/0063163 A1    Mar. 14, 2013

(30) Foreign Application Priority Data

Sep. 9, 2011    (JP) ................... 2011-196916

(51) Int. Cl.
*G01R 27/26* (2006.01)
*G01N 27/22* (2006.01)
*G01K 7/34* (2006.01)

(52) U.S. Cl.
CPC ............ *G01N 27/223* (2013.01); *G01N 27/225* (2013.01); *G01N 27/22* (2013.01); *G01K 7/34* (2013.01)

(58) Field of Classification Search
CPC ... G01N 27/223; G01N 27/22; G01N 27/225; G01D 5/2417; G01K 7/34
USPC ............ 324/76.11–76.83, 600, 649, 658, 663
See application file for complete search history.

(56) References Cited

U.S. PATENT DOCUMENTS

| 5,846,870 | A | 12/1998 | Ishida et al. |
| 6,313,033 | B1 | 11/2001 | Chiang et al. |
| 6,376,939 | B1 * | 4/2002 | Suzuki et al. ................. 307/326 |
| 2003/0000312 | A1 * | 1/2003 | Ono ................................ 73/753 |
| 2003/0057968 | A1 * | 3/2003 | Wang et al. .................... 324/690 |
| 2003/0179805 | A1 * | 9/2003 | Hamamoto et al. ............ 374/16 |
| 2005/0247114 | A1 * | 11/2005 | Kahn et al. ................... 73/53.01 |

(Continued)

FOREIGN PATENT DOCUMENTS

| CN | 101505812 | 8/2009 |
| JP | H05-72157 | 3/1993 |
| JP | H6-94663 | 4/1994 |

(Continued)

OTHER PUBLICATIONS

WO 2011046119 Machine Translation.*

(Continued)

*Primary Examiner* — Tung X Nguyen
*Assistant Examiner* — Raul Rios Russo
(74) *Attorney, Agent, or Firm* — Troutman Sanders LLP

(57) ABSTRACT

A humidity sensor according to the present examples include a sensor portion for detecting humidity in the ambient environment, and a power supply portion for applying an AC voltage to the sensor portion, wherein the sensor portion is structured so as to have an impedance that is higher than a sensor portion of a conventional humidity sensor. As a result, it is possible to reduce the amount of power consumed in the sensor portion when compared to that of a conventional humidity sensor. Doing so makes it possible to reduce the amount of electrical power consumed in the humidity sensor as a whole in the present invention, including the sensor portion, when compared to that of a conventional humidity sensor.

6 Claims, 16 Drawing Sheets

(56) References Cited

U.S. PATENT DOCUMENTS

| | | | |
|---|---|---|---|
| 2006/0105467 A1* | 5/2006 | Niksa et al. | 436/150 |
| 2008/0041792 A1 | 2/2008 | Crnkovich et al. | |
| 2009/0322543 A1 | 12/2009 | Crnkovich et al. | |
| 2010/0332156 A1* | 12/2010 | Shimakata et al. | 702/50 |
| 2011/0011179 A1* | 1/2011 | Gustafsson et al. | 73/335.03 |
| 2012/0206147 A1 | 8/2012 | Sim et al. | |

FOREIGN PATENT DOCUMENTS

| | | |
|---|---|---|
| JP | H10-163445 | 6/1998 |
| JP | 2001-102548 | 4/2001 |
| JP | 2001-249100 | 9/2001 |
| JP | 2009-019964 | 1/2009 |
| JP | 2011-094979 | 5/2011 |
| WO | 2009/008237 | 1/2009 |
| WO | 2011/046119 | 4/2011 |

OTHER PUBLICATIONS

Chinese Office Action dated Apr. 22, 2014, from corresponding Chinese Application No. 201210324079.4.

De-Liang Ning, et al. "Structure design of novel type capacitance sensor for steam humidity" 2007, Transducer and Microsystem Technologies 26(3), pp. 65-67, 72.

Jia Liu, et al. "Structural optimization of capacitive humidity sensor" 2009, Applied Science and Technology, vol. 36, No. 6, pp. 43-44, 52.

Wenshun Meng, et al. "Principle and Application of Capacity Sensor" 2003, Modern Electronic Technique, pp. 78-81.

Japanese Office Action dated Oct. 10, 2014, which issued during prosecution of Japanese Application No. 2011-196916, which corresponds to the present application.

Korean Office Action dated Sep. 24, 2014, which issued during prosecution of Korean Application No. 10-2012-0086314, which corresponds to the present application.

* cited by examiner

ENVIRONMENT SENSOR

CROSS-REFERENCE TO RELATED APPLICATION

This application claims priority to Japanese Patent Application 2011-196916, filed Sep. 9, 2011. The entirety of this application is incorporated herein by reference.

FIELD OF TECHNOLOGY

Several forms of the present invention relates to an environment sensor for detecting the physical quantities in the environment.

BACKGROUND

Conventionally humidity sensors wherein a humidity-sensitive film has been interposed between two electrodes have been known as sensors of this type. (See, for example, Japanese Unexamined Patent Application Publication H6-94663 ("JP '663").) In this type of humidity sensor, the electrostatic capacitance value of the humidity-sensitive film varies in accordance with the humidity within the measurement environment. Because of that, it is possible to convert (calculate) the detected electrostatic capacitance value into a humidity level if the correspondence relationship between the humidity and the electrostatic capacitance value is known in advance.

Moreover, in addition to environment sensors of an electrostatic capacitance type, described in JP '663, there are also known environment sensors for detecting physical quantities in the environment using methods such as a heat type, an optical type, a chemical type, and an electrical type.

Note that in these conventional environment sensors, typically the amount of electrical power assumed has not been an issue because they have been supplied electrical power from so-called fixed power supplies. However, in recent years there has been an increasing need to detect physical quantities in a variety of different environments, and it has been desirable to reduce the amount of power consumed by the environment sensor in devices wherein there are limitations to the amount of power from the power supply, such as in mobile or portable devices.

Several situations for the present examples have been considered for the problem set forth above, and one object is to provide an environment sensor able to reduce the amount of power consumed.

SUMMARY

The environment sensor according to examples of the present invention includes a sensor portion for detecting a specific physical quantity in the environment; and a power supply portion for applying an AC voltage to the sensor portion, wherein: the sensor portion is structured so as to have an impedance that is higher than a sensor portion of a conventional environment sensor.

Given this structure, the impedance in the sensor portion to which the AC voltage is applied is higher than that of a conventional environment sensor. As a result, it is possible to reduce the amount of power consumed in the sensor portion when compared to that of a conventional environment sensor.

Preferably the sensor portion is structured including a first electrode plate, a second electrode plate, and a dielectric that is disposed between the first electrode plate and the second electrode plate, so that the electrostatic capacitance between the first electrode plate and the second electrode plate can change in accordance with the specific physical quantity in the environment; the power supply portion applies the AC voltage between the first electrode plate and the second electrode plate; and the distance between the first electrode plate and the second electrode plate, and the surface areas of the first electrode plate and the second electrode plate, are set depending on the impedance of sensor portion.

In this structure, the distance between the first electrode plate and the second electrode plate and the areas of the first electrode plate and the second electrode plate are set based on the impedance of the sensor portion. If there is a sensor portion with a distance $d_1$ between the two electrode plates, surface areas $S_1$ of the two electrode plates, a humidity sensitivity factor $D_h$, and an electrostatic capacitance $C_1$ (=$D_h \times S_1/d_1$) in a conventional environment sensor of an electrostatic capacitance type wherein the electrostatic capacitance varies in accordance with a specific physical quantity, then the electrostatic capacitance $C_h$ of the sensor portion can be made smaller than the electrostatic capacitance $C_1$ ($C_h < C_1$), and the impedance $Z_k$ of the sensor portion in the present invention can be made higher than the impedance $Z_1$ of the sensor portion of the conventional environment sensor ($Z_h > Z_1$) through setting the distance $d_h$ between the first electrode plate and the second electrode plate in the environment sensor according to examples of the present invention to be larger than the distance $d_1$ ($d_h > d_1$), setting the surface areas $S_h$ of the first electrode plate and the second electrode plate in the environment sensor according to the examples of the present invention to be smaller than the surface area $S_1$ ($S_h < S_1$), or both. Consequently, it is possible to cause the electrostatic capacitance $C_h$ of the sensor portion according to examples of the present invention to be less than that of the electrostatic capacitance $C_1$ of the sensor portion of the conventional environment sensor through setting the distance $d_h$ and the surface areas $S_h$ based on the impedance $Z_h$ of the sensor portion, to make it possible to cause the impedance $Z_h$ of the sensor portion in the present invention to be higher than the impedance $Z_1$ of the sensor portion of the conventional environment sensor. This makes it possible to achieve (structure) the environment sensor according to the examples of the present invention easily.

Preferably, the surface of the first electrode plate on the dielectric side is formed with a plurality of recessed portions and raised portions.

In this structure, the surface of the first electrode plate on the dielectric side is formed with a plurality of recessed portions and raised portions. Here there is a problem with the dielectric swelling and having a reduction (degradation) in sensitivity to humidity in the conventional environment sensor when disposed in a high-humidity environment or when a specific amount of time (months) has elapsed since use. Moreover, there has been the risk of delamination (peeling) of the dielectric from the electrode plate due to the stress due to swelling (expansion) of the dielectric. In contrast, in the environment sensor according to the examples of the present invention, the formation of the recessed portions and raised portions in the surface of the first electrode plate on the dielectric side increases the surface area of the surface of the first electrode plate on the dielectric side. Doing so enables a mitigation of the per-unit-surface-area force that acts on the dielectric, when compared to the case wherein the recessed and raised portions are not formed on the surface of the first electrode plate on the dielectric side, not only reducing the likelihood of delamination of the dielectric, but also making it possible to suppress the reduction (degradation) of sensitivity caused by the swelling of the dielectric, thereby enabling stable detection over an extended period of time. Moreover, in particular, this enables an increase in the detection sensitivity of the electrostatic capacitance $C_h$ when the surface area $S_h$ of the first electrode plate has been set so as to be small, based on the impedance $Z_h$ of the sensor portion.

Preferably a coupling layer for bonding the dielectric is further provided on the dielectric side of the first electrode plate.

This structure further provides a coupling layer, for bonding the dielectric, on the surface of the first electrode plate on the dielectric side. This increases the adhesion between the first electrode plate and the dielectric, thereby not only reducing the likelihood of delamination of the dielectric, but enabling the suppression of the reduction in sensitivity due to swelling of the dielectric. This enables stable detection over an extended period of time.

Preferably, a substrate for supporting the first electrode plate is further provided.

In this structure, a substrate for supporting the first electrode plate is further provided. This makes it possible to reinforce the mechanical strength of the first electrode plate, and, in particular, is effective when the surface area $S_h$ of the first electrode plate is set to be small based on the impedance $Z_h$ of the sensor portion.

Preferably a controlling portion for driving the power supply portion intermittently is further provided.

In this structure, a controlling portion for driving the power supply portion intermittently is further provided. Doing so enables a further reduction in the amount of electrical power consumed by the environment sensor when compared to the case of driving the power supply portion continuously so as to always supply power to the sensor portion. Moreover, in the environment sensor according to the examples of the present invention, the electrostatic capacitance $C_h$ is set so as to be smaller than the electrostatic capacitance $C_1$ of the conventional environment sensor, based on the impedance $Z_h$ of the sensor portion, and thus, if the internal resistance $R_{if}$ is the same, then the time constant $\tau_h$ of the environment sensor according to the examples of the present invention is smaller than the time constant $\tau_1$ of the conventional environment sensor ($\tau_h < \tau_1$). Consequently, the controlling portion driving intermittently the power supply portion that applies the AC voltage between the first electrode plate and the second electrode plate enables a shortening of the time before reaching a steady state, that is, a shortening of the waiting time (the stabilization time) prior to starting or stopping the sensor portion. This makes it possible to reduce the amount of electrical power consumed during this waiting time, enabling a further decrease in the amount of electrical power consumed in the environment sensor according to examples of the present invention, when compared to the conventional environment sensor.

Preferably an interface circuit portion for detecting the electrostatic capacitance, which includes the power supply portion, and a communicating portion for sending, to the outside, the electrostatic capacitance detected by the interface circuit portion, are further provided.

In this structure, an interface circuit portion for detecting the aforementioned electrostatic capacitance, and a communicating portion for sending, to the outside, the electrostatic capacitance that has been detected, are further provided within the power supply portion. As a result, an electrostatic capacitance that varies depending on the specific physical quantity is sent to the outside. This makes it possible to communicate (provide notification) the specific physical quantity detected by the sensor portion to a device on the outside.

The environment sensor according to the examples of the present invention, when compared to a conventional environment sensor, is able to reduce the amount of electrical power consumed in the sensor portion. Doing so enables a reduction in the overall amount of electrical power consumed in the environment sensor according to the examples, which includes the sensor portion, when compared to the conventional environment sensor. Moreover, the environment sensor according to the examples of the present invention may be applied well to not only devices with fixed power supplies, but also devices that are supplied with power from mobile power supplies or batteries, energy harvesting devices (environmental electrical power generators) that generate their own electricity through weak energy such as, for example, solar power electric generation, a temperature differential electric generation, vibrational electric generation, bioelectric generation, airflow or wind-power electric generation, hydropower electric generation, wave power electric generation, rotary electric generation, or the like, and also to devices that are provided with mobile fuel cells, and, in particular, to devices that perform wireless communications that are mobile or portable.

DETAILED DESCRIPTION

Examples of the present invention are described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions. Moreover, in the explanations below the top of the figure shall be defined as "up," the bottom of the figure shall be defined as "down," the left side of the figure shall be defined as "left," and the right side of the figure shall be defined as "right."

FIG. 1 through FIG. 16 illustrate an example of an environmental sensor according to the present invention. In the present example, a humidity sensor for detecting humidity in the air surrounding the measurement environment is explained as an example of an environment sensor for detecting a specific physical quantity in the environment.

Figure 1:
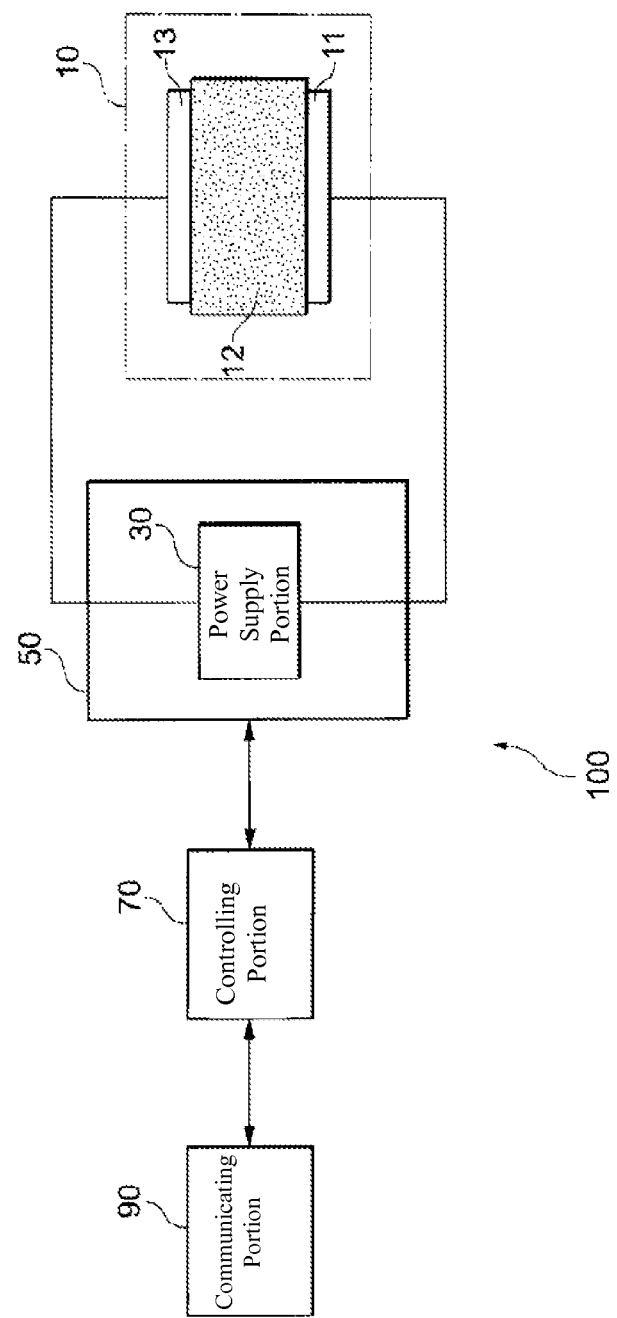
FIG. 1 is a block diagram for explaining a humidity sensor in a form of an example.

FIG. 1 is a block diagram for explaining a humidity sensor in an example. As illustrated in FIG. 1, a humidity sensor 100 is disposed in the environment that is subject to detection, and is for detecting the humidity in the environment (in the atmosphere). The humidity sensor 100 is provided with a sensor portion 10, an interface circuit portion 50, a controlling portion 70, and a communicating portion 90.

The sensor portion 10 includes a first electrode plate 11, a second electrode plate 13, and a humidity-sensitive film 12 disposed between the first electrode plate 11 and the second electrode plate 13, to function as a capacitor that is able to store charge between the first electrode plate 11 and the second electrode plate 13. Note that the humidity-sensitive film 12 in the present example corresponds to one example of a "dielectric" in the environment sensor according to the present invention.

Typically in a capacitor the electrostatic capacitance C is expressed by the following Equation (1) when the distance between the two electrode plates is $d(m)$, the surface areas of the two electrode plates are $S(m^2)$, and the dielectric constant of the dielectric is $\in$ (F/m):

$$C(F) = \in \times S/d \qquad (1)$$

In the humidity-sensitive film 12, the humidity sensitivity factor $D_h$, which includes the dielectric constant $\in$, varies in accordance with the ambient humidity.

Because of this, the electrostatic capacitance of the sensor portion 10 can vary in accordance with the ambient humidity. Consequently, the electrostatic capacitance Ch of the sensor portion 10 can be expressed by Equation (2), below, using the humidity sensitivity factor Dh when there is a distance dh between the first electrode plate 11 and the second electrode plate 13 and the surface areas of the first electrode plate 11 and the second electrode plate 13 are $S_h$:

$$C_h = D_h \times S_h / d_h \qquad (2)$$

The interface circuit portion 50 includes the power supply portion 30. The power supply portion 30 is connected electrically to the first electrode plate 11 and the second electrode plate 13, and applies an AC voltage between the first electrode plate 11 and the second electrode plate 13. Doing so produces an electric current that flows in the sensor portion 10 in accordance with the electrostatic capacitance $C_h$, and the interface circuit portion 50 detects the electrostatic capacitance $C_h$ of the sensor portion 10 based on this electric current signal. Moreover, because the electrostatic capacitance $C_h$ of the sensor portion 10 varies in accordance with the ambient humidity, this makes it possible to detect the ambient humidity based on the electric current signal.

In the sensor portion 10 to which the AC voltage is applied, the impedance $Z_h$ is given by Equation (3), below:

$$Z_h = 1/2\pi f C_h \qquad (3)$$

Note that f represents the frequency of the AC voltage.

Moreover, the relationship in Equation (4), below, is satisfied when the voltage applied between the first electrode plate 11 and the second electrode plate 13 and the electric current that flows between the first electrode plate 11 and the second electrode plate 13 are represented by $e_h(t)$ and $i_h(t)$, where each are a function of time t:

$$e_h(t) = Z_h \cdot i_h(t) \qquad (4)$$

As described above, the ambient humidity can be detected when the power supply portion 30 applies an AC voltage between the first electrode plate 11 and the second electrode plate 13. On the other hand, when there is an electric current that flows between the first electrode plate 11 and the second electrode plate 13, electrical power is consumed within the sensor portion 10. The electrical power consumption $p_h(t)$ of the sensor portion 10 can be expressed by the following Equation (5) using the impedance $Z_h$:

$$p_h(t) = e_h(t) \cdot i_h(t) = e_h(t)^2 / Z_h \qquad (5)$$

As shown in Equation (5), the electrical power consumption $p_h(t)$ is proportional to the inverse of the impedance $Z_h$ (that is, is inversely proportional), and thus increasing the value for the impedance $Z_h$ decreases the value of the electrical power consumption $p_h(t)$, that is, decreases the amount of electrical power consumed.

Moreover, as shown in Equation (3), the impedance $Z_h$ is proportional to the inverse of the frequency f and the electrostatic capacitance $C_h$ (that is, inversely proportional), and thus reducing the value of the frequency f and/or the electrostatic capacitance $C_h$ increases the impedance $Z_h$.

Moreover, as shown in Equation (2) not only is the electrostatic capacitance $C_h$ proportional to the inverse of the distance $d_h$ (that is, inversely proportional), but is proportional to the surface area $S_h$, so the value for the electrostatic capacitance $C_h$ is decreased by increasing the distance $d_h$ and/or decreasing the surface area $S_h$.

The sensor portion 10 to which the AC voltage is applied in the present example is structured so that the impedance is higher than in the sensor portion of a conventional environment sensor. As a result, it is possible to reduce the amount of power consumed in the sensor portion 10 when compared to that of a conventional environment sensor.

Specifically, the distance $d_h$ between the first electrode plate 11 and the second electrode plate 13, and the surface areas $S_h$ of the first electrode plate 11 and the second electrode plate 13, are set based on the impedance $Z_h$ of the sensor portion 10.

If there is a sensor portion with a distance $d_1$ between the two electrode plates, surface areas $S_1$ of the two electrode plates, a humidity sensitivity factor $D_h$, and an electrostatic capacitance $C_1$ (=$D_h \times S_1/d_1$) in a conventional humidity sensor of an electrostatic capacitance type wherein the electrostatic capacitance varies in accordance with the humidity, then the electrostatic capacitance $C_h$ of the sensor portion can be made smaller than the electrostatic capacitance $C_1$ ($C_h < C_1$), and the impedance $Z_h$ of the sensor portion 10 in the examples of the present invention are made higher than the impedance $Z_1$ of the sensor portion of the conventional humidity sensor ($Z_h > Z_1$) through setting the distance $d_h$ between the two plates in the humidity sensor 100 according to the present examples to be larger than the distance $d_1$ ($d_h > d_1$), setting the surface areas $S_h$ in the humidity sensor 100 according to the present example to be smaller than the surface area $S_1$ ($S_h < S_1$) or to an appropriate value, or both. Consequently, it is possible to cause the electrostatic capacitance $C_h$ of the sensor portion 10 according to the present example to be less than that of the electrostatic capacitance $C_1$ of the sensor portion of the conventional humidity sensor through setting the distance $d_h$ and the surface areas $S_h$ based on the impedance $Z_h$ of the sensor portion 10, to make it possible to cause the impedance $Z_h$ of the sensor portion 10 in the present example to be higher than the impedance $Z_1$ of the sensor portion of the conventional humidity sensor.

A controlling portion 70 is connected electrically to the interface circuit portion 50, to output a driving signal with each specific time interval to drive (that is, to start and stop) intermittently the interface circuit portion 50 that includes the power supply portion 30. Doing so enables a further reduction in the amount of electrical power consumed by the humidity sensor 100, when compared to the case of the sensor portion 10 wherein the power supply portion 30 is driven continuously so that the sensor portion 10 is always supplied power.

Typically an unintended internal resistance $R_{if}$ exists within an electric circuit, and thus, in consideration of this resistive component, the impedance $Z_{if}$ of the sensor portion 10 is expressed by Equation (6), below:

$$Z_{if} = R_{if} + Z_h \quad (6)$$

Additionally, the voltage $e_h(t)$ of the sensor portion 10 is expressed by Equation (7), below:

$$e_h(t) = E_{ex} * \exp^{\frac{-t}{C_h R_{if}}} \quad (7)$$

Note that $E_{ex}$ represents the effective value of the voltage.

Consequently from Equation (7), the time constant $\tau_h$ of the sensor portion 10 is given by Equation (8), below:

$$\tau_h = C_h \cdot R_{if} \quad (8).$$

The time constant is an index that expresses the response speed in the electric signal, and is the time for the voltage signal or current signal to reach about 63.2(%) or about 36.8 (%) of the steady-state value. At this time, the smaller the time constant τh when intermittently driving the interface circuit portion 50 by the controlling portion 70, the more quickly the sensor portion 10 achieves the steady state.

Figure 2:
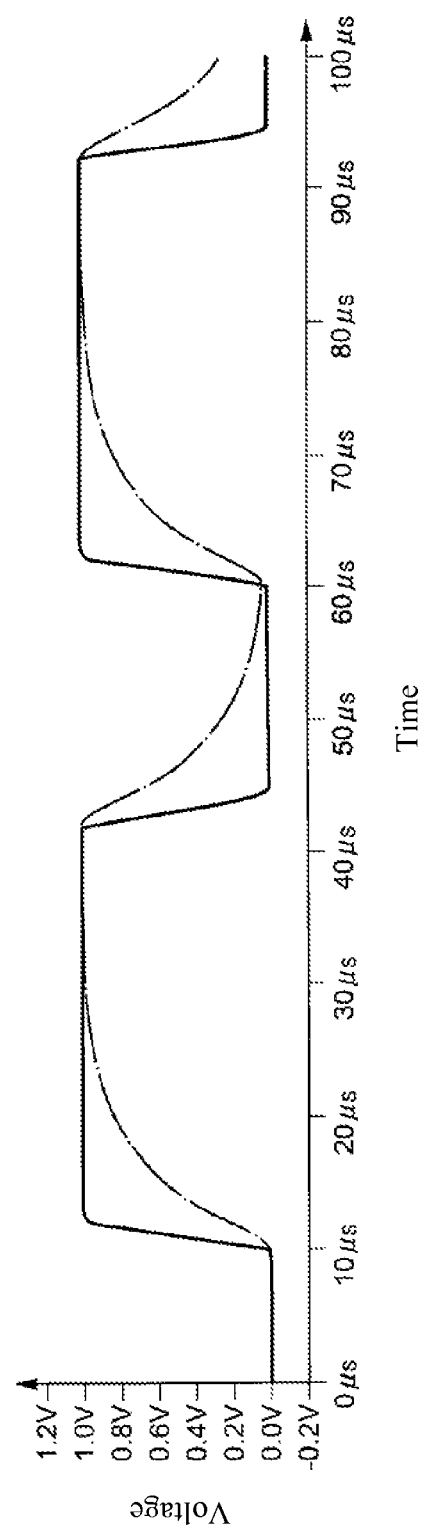
FIG. 2 is a graph illustrating one example of changes in voltages over time in intermittent driving.
Figure 3:
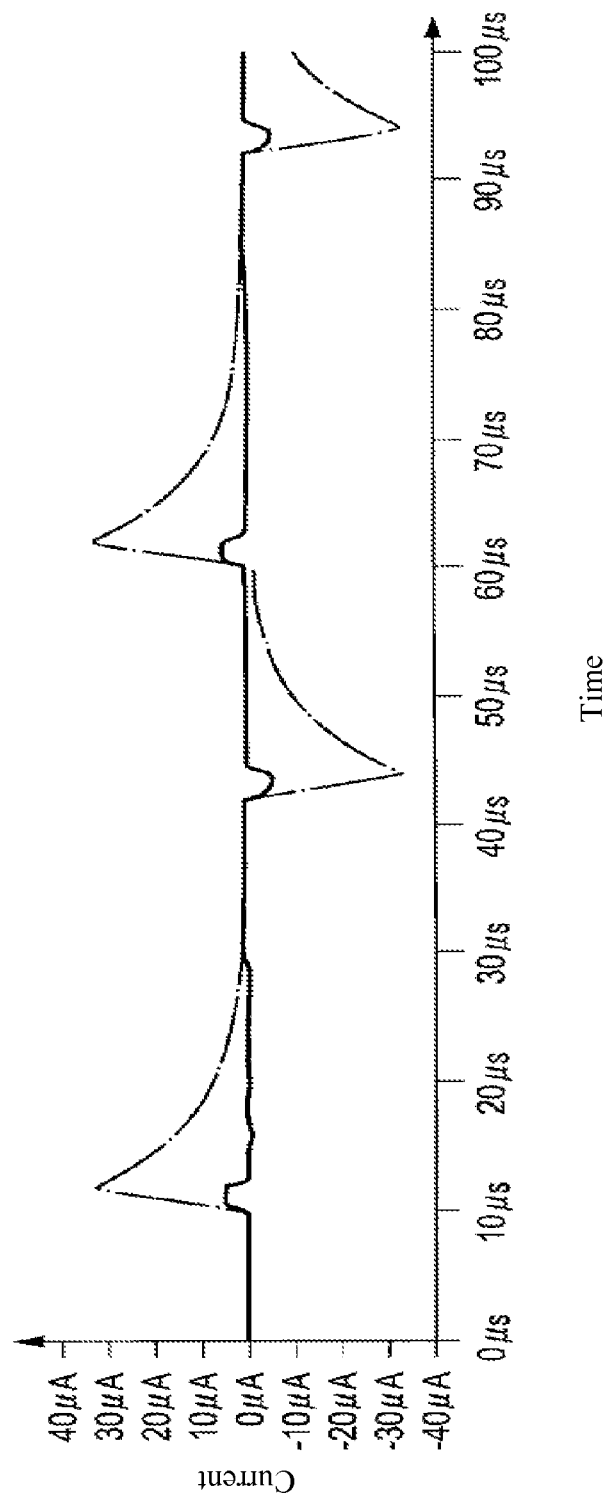
FIG. 3 is a graph illustrating one example of currents in voltages over time in intermittent driving.

FIG. 2 is a graph illustrating one example of the changes in voltage over time in intermittent driving, and FIG. 3 is a graph showing one example of the changes over time in current in intermittent driving. Note that in FIG. 2 and FIG. 3, the solid lines represent the case wherein the electrostatic capacitance Ch is in the order of tens of pF in the humidity sensor 100 in the present example, and the dotted line represents a case where in the electrostatic capacitance C1 is in the order of hundreds of pF in the conventional electrostatic capacitance humidity sensor. Note that for ease in comparison, in both cases the internal resistances Rif are set identically to be extremely small. As shown in FIG. 2 and FIG. 3, it can be seen that, when compared to the case wherein the electrostatic capacitance C1 is in the order of hundreds of pF, the rise is faster when starting up the intermittent driving, and the fall is faster when stopping, when the electrostatic capacitance Ch is in the order of tens of pF.

Note that while FIG. 2 and FIG. 3 show the case wherein the time interval for intermittent driving is in the order of tens of μs, there is no limitation thereto. Depending on the application, the time interval for intermittent driving may be several seconds, several minutes, or even longer.

Because here the electrostatic capacitance $C_h$ in the humidity sensor 100 according to the present example is set, based on the impedance $Z_h$ of the sensor portion 10, to be smaller than the electrostatic capacitance $C_1$ of the conventional humidity sensor (that is, $C_h < C_1$), and thus if the internal resistance $R_{if}$ is the same, the time constant $\tau_h$ of the humidity sensor 100 according to the present example can be smaller than the time constant $\tau_1$ of the conventional humidity sensor (that is, $\tau_h < \tau_1$). As a result, this makes it possible to shorten the time until the steady state is achieved, that is, to shorten the wait time (the stabilization time) until the sensor portion 10 starts up or is stopped, in intermittent driving of the interface circuit portion 50, which includes the power supply portion 30, by the controlling portion 70.

The communicating portion 90, illustrated in FIG. 1, is connected electrically to the controlling portion 70, and inputs, through the controlling portion 70, the electrostatic capacitance Ch of the sensor portion 10 that has been detected by the interface circuit portion 50. The communicating portion 90 sends the inputted electrostatic capacitance Ch to an external device using either a wireless communication method or a wired communication method. As a result, the electrostatic capacitance $C_h$, which varies in accordance with the ambient humidity, is sent to the outside.

The structure of the sensor portion 10, illustrated in FIG. 1, is explained in detail next.

Figure 4:
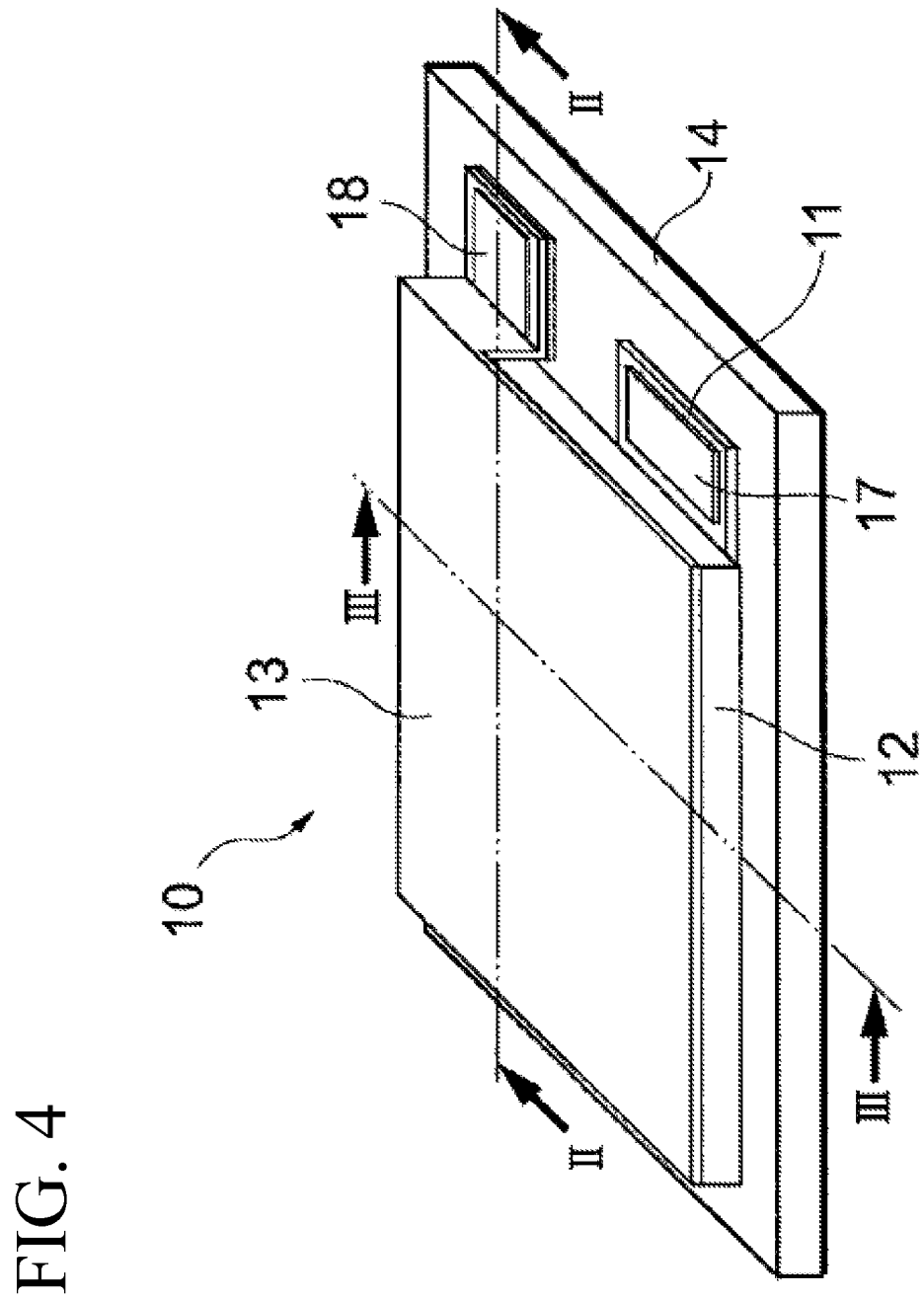
FIG. 4 is a perspective diagram for explaining an example of the sensor portion shown in FIG. 1.
Figure 5:
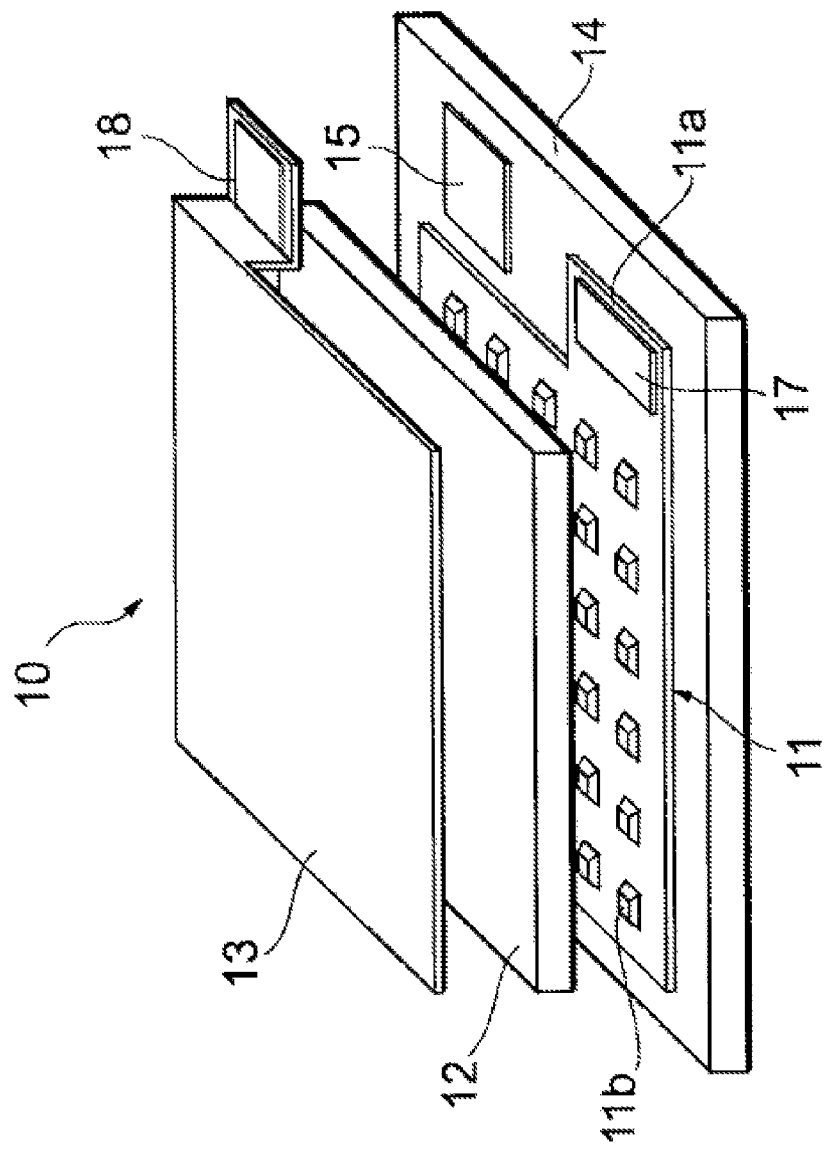
FIG. 5 is an assembly perspective diagram of the sensor portion shown in FIG. 4.

FIG. 4 is a perspective diagram for explaining an example of the sensor portion 10 shown in FIG. 1, and FIG. 5 is an assembly perspective diagram of the sensor portion 10 illustrated in FIG. 4. As shown in FIG. 4 and FIG. 5, the first electrode plate 11 is disposed on the top face of a substrate 14, and is supported by the substrate 14. This enables the mechanical strength of the first electrode plate 11 to be reinforced, and is particularly effective in the case wherein the surface area $S_h$ of the first electrode plate 11 is set so as to be small, based on the impedance $Z_h$ of the sensor portion 10.

The substrate 14 is structured from an insulating material such as, for example, silicon, glass, ceramic, sapphire, quartz, or the like. The first electrode plate 11, which includes a first connecting terminal 11a, and an underlying electrode 15, which is disposed separated from the first electrode plate 11, are disposed on the top face of the substrate 14.

The first electrode plate 11 is structured from a metal layer comprising at least one layer of platinum/gold/niobium (Pt/Au/Nb), platinum/chrome (Pt/Cr), platinum/niobium (Pt/Nb), platinum/titanium (Pt/Ti), nickel (Ni), aluminum (Al), copper (Cu), or the like. The first electrode plate 11 may be formed through, for example, a vapor deposition method, a sputtering method, or the like, to deposit the aforementioned metal layer onto the substrate 14, followed by patterning, lift-off, or metal masking. The thickness of the first electrode plate 11, formed in this way, may be, for example, between several hundred nanometers (or several thousand angstroms) and 1 μm.

Figure 6:
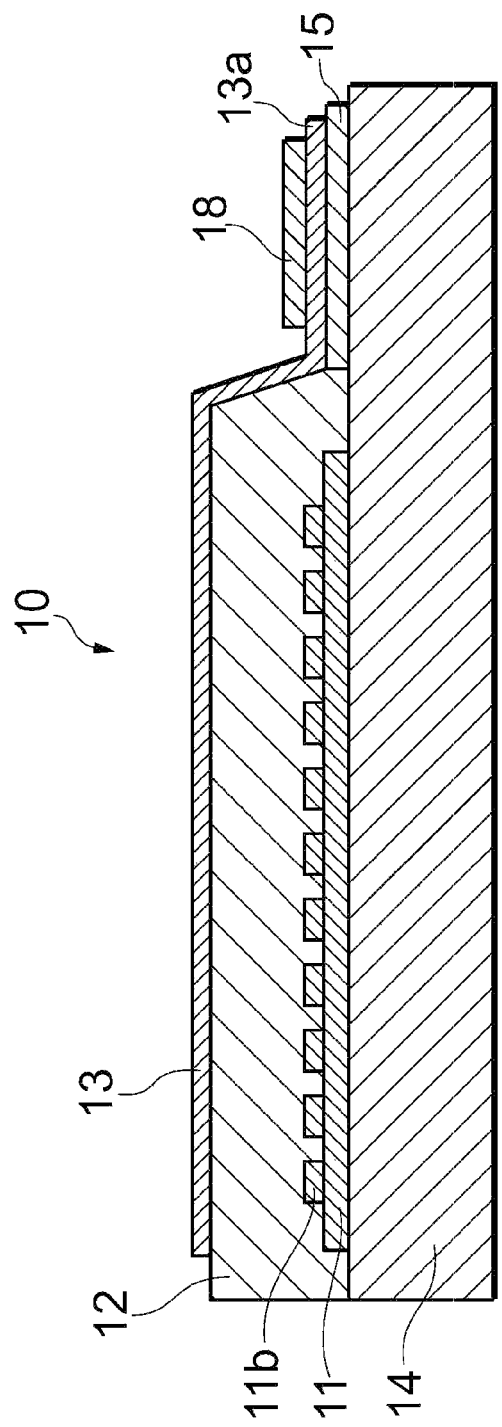
FIG. 6 is a cross-sectional diagram viewed in the direction of the arrow in the line II-II in FIG. 4.
Figure 7:
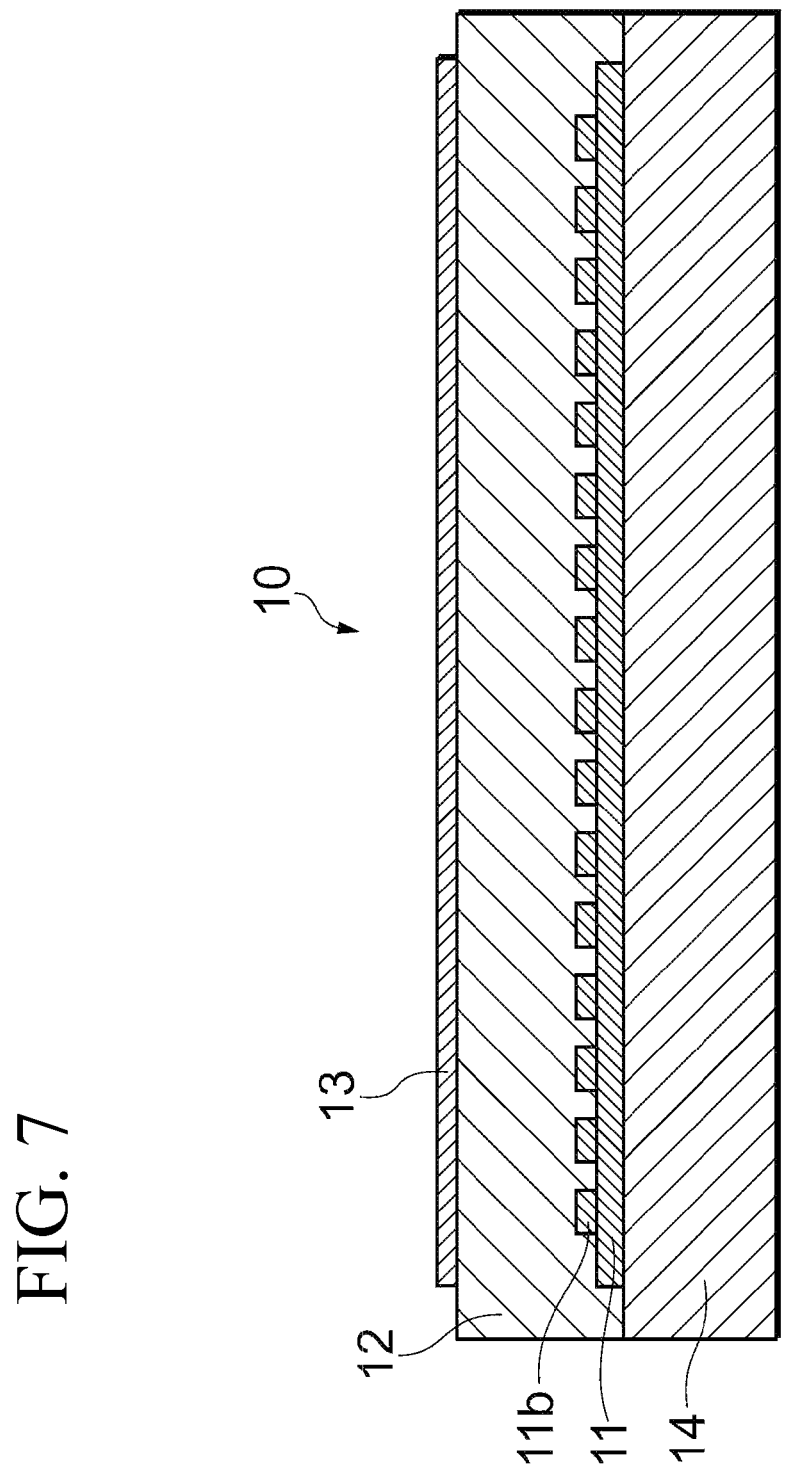
FIG. 7 is a cross-sectional diagram viewed in the direction of the arrow in the line III-III in FIG. 4.

FIG. 6 is a cross-sectional diagram in the direction of the arrow II-II shown in FIG. 4, and FIG. 7 is a cross-sectional diagram in the direction of the arrow III-III shown in FIG. 4. As shown in FIG. 6 and FIG. 7, a plurality of raised portions 11b is provided on the flat top face of the first electrode plate 11, to form a plurality of recessed portions and raised portions in the surface that contacts the humidity-sensitive film 12.

The plurality of raised portions 11b is formed using, for example, chemical etching, a dry etching method, including the reactive ion etching (RIE) method, or a micro-machining technology (an MEMS technology), including the lift-off method, or the like.

While FIG. 6 and FIG. 7 show examples wherein a plurality of raised portions 11b is disposed on the top face of the first electrode plate 11, there is no limitation thereto. Other structures may be used instead insofar as the result is the formation of a plurality of recessed and raised portions on the surface of the first electrode plate 11 on the humidity-sensitive film 12 side.

Figure 8:
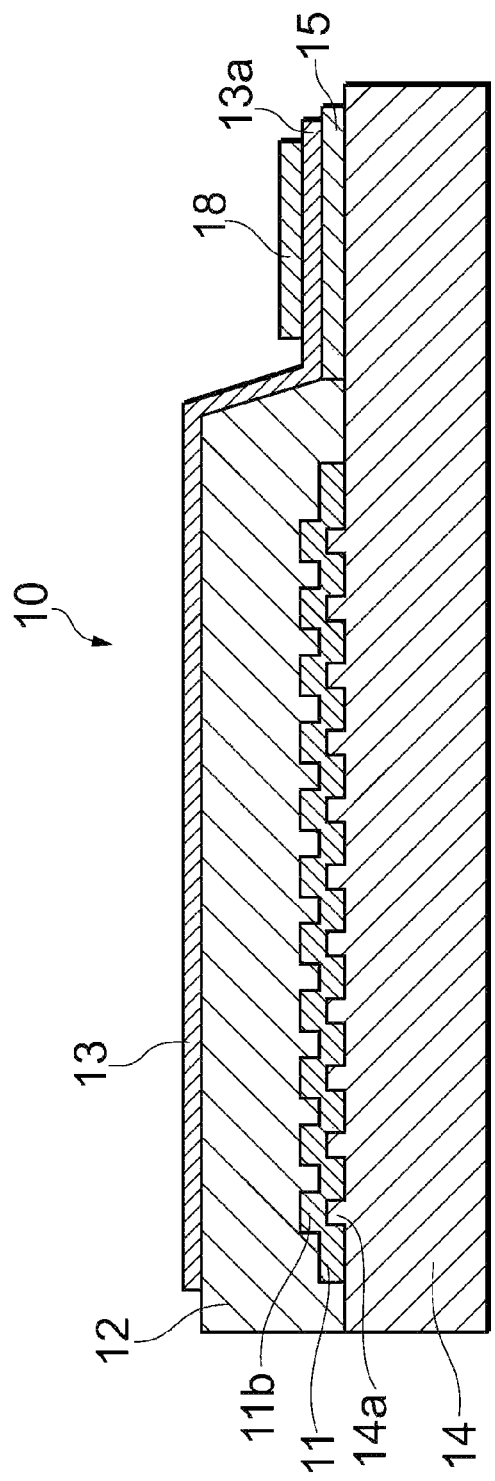
FIG. 8 is a cross-section sectional diagram for explaining an alternate example of the sensor portion shown in FIG. 4.
Figure 9:
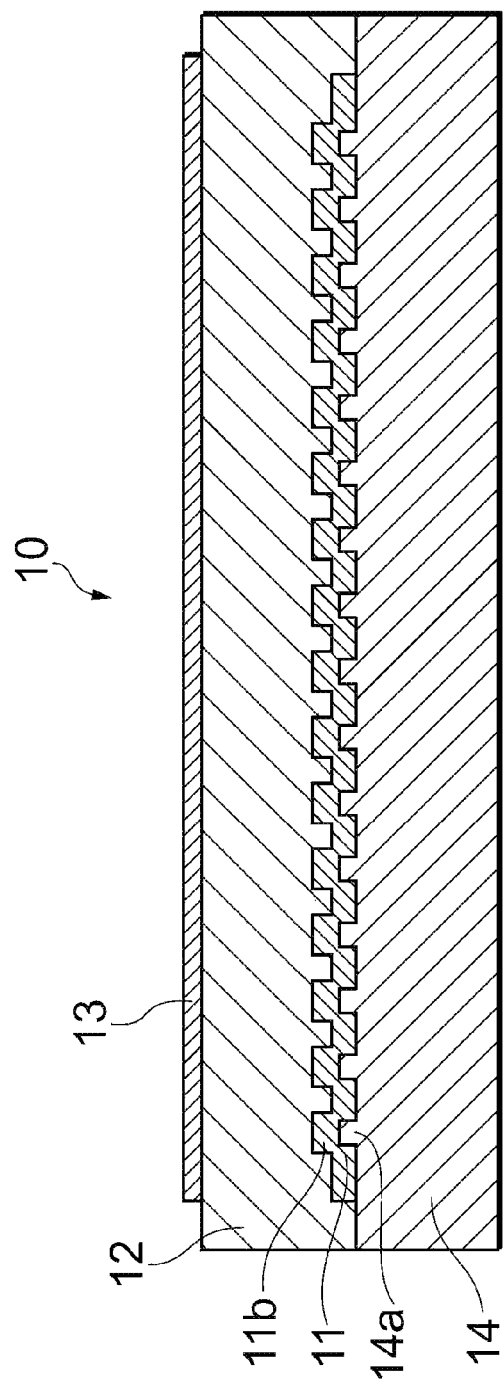
FIG. 9 is a cross-section sectional diagram for explaining an alternate example of the sensor portion shown in FIG. 4.

FIG. 8 and FIG. 9 are cross-sectional diagrams for explaining an alternate example of the sensor portion 10 shown in FIG. 4. Note that as with FIG. 6, FIG. 8 is a cross-sectional diagram in the direction of the arrow II-II shown in FIG. 4, and, as with FIG. 7, FIG. 9 is a cross-sectional drawing in the direction of the arrow III-III shown in FIG. 4. As shown in FIG. 8 and FIG. 9, a plurality of raised portions 14a may be provided on the top face of the substrate 14 together with the provision of the plurality of raised portions 11b on the top face of the first electrode plate 11.

Depending on the material of the substrate 14, the raised portions 14a may be formed using, for example, a chemical etching method, a dry etching method, a reactive ion etching (RIE) method, or a micro-machining technology (an MEMS technology) such as a laser machining method, or a machining technology such as a sandblasting method, a thin film deposition technology such as epitaxial deposition, or a film depositing technology such as vapor deposition or a sputtering method, or the like.

Figure 10:
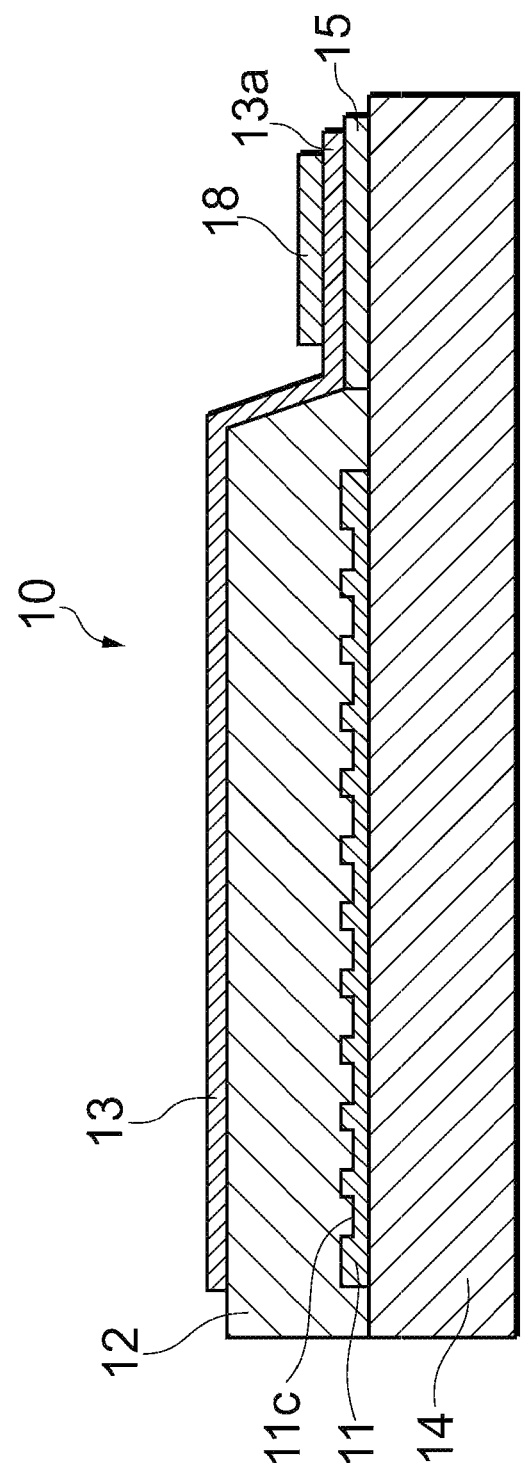
FIG. 10 is a cross-section sectional diagram for explaining another example of the sensor portion shown in FIG. 4.
Figure 11:
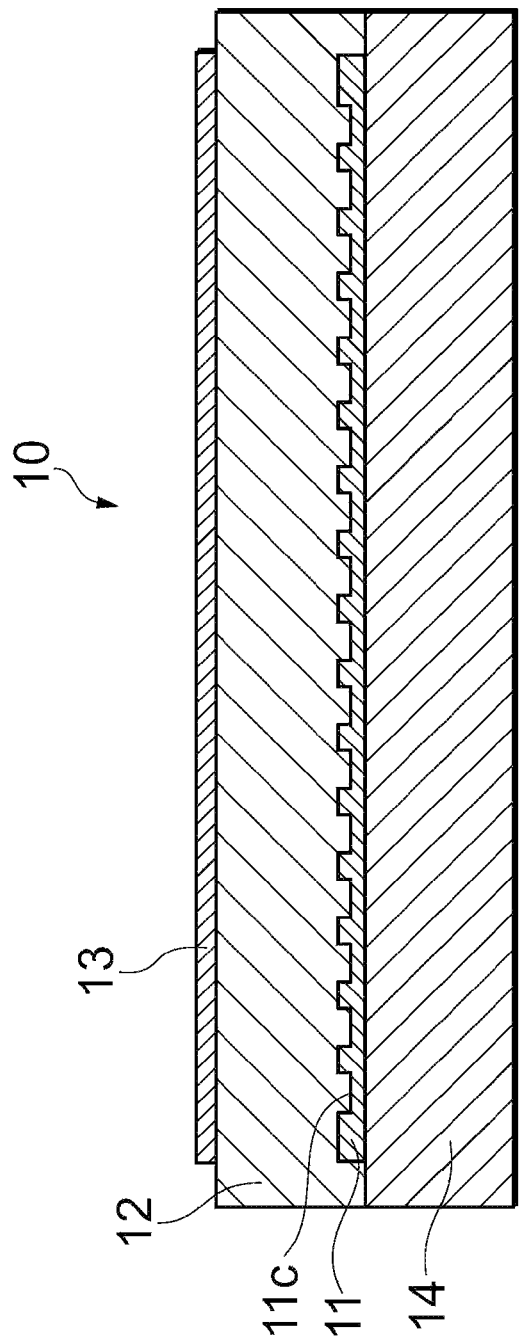
FIG. 11 is a cross-section sectional diagram for explaining another example of the sensor portion shown in FIG. 4.

FIG. 10 and FIG. 11 are cross-sectional diagrams for explaining another example of the sensor portion 10 shown in FIG. 4. Note that as with FIG. 6, FIG. 10 is a cross-sectional diagram in the direction of the arrow II-II shown in FIG. 4, and, as with FIG. 7, FIG. 11 is a cross-sectional drawing in the direction of the arrow III-III shown in FIG. 4. As shown in FIG. 10 and FIG. 11, a plurality of recessed portions 11c may be provided, instead of the plurality of raised portions 11b, on the top face of the first electrode plate 11. In this case as well, similarly recessed portions are formed on the surface of the first electrode plate 11 on the humidity-sensitive film 12 side.

As with the case of forming the raised portions 11b, the recessed portions 11c may be formed through, for example, a chemical etching method, a dry etching method, a reactive etching (RIE) method, or a micro-machining technology (an MEMS technology) such as the lift-off method.

Figure 12:
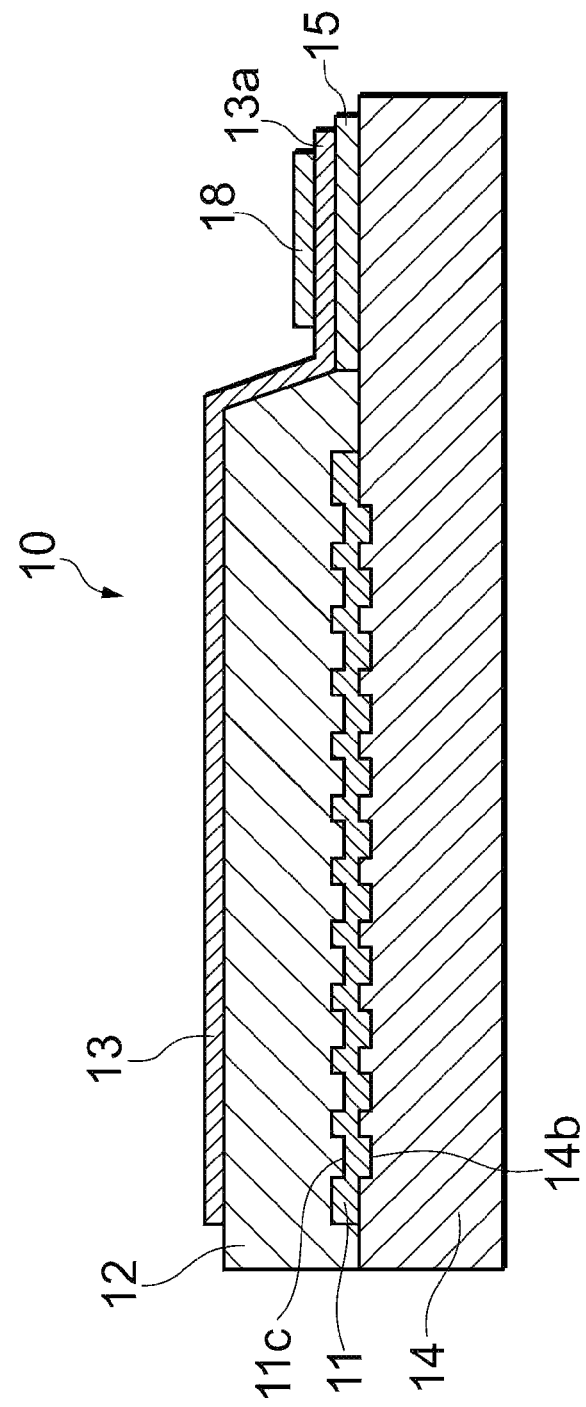
FIG. 12 is a cross-section sectional diagram for explaining an alternate example of the sensor portion shown in FIG. 10 and FIG. 11.
Figure 13:
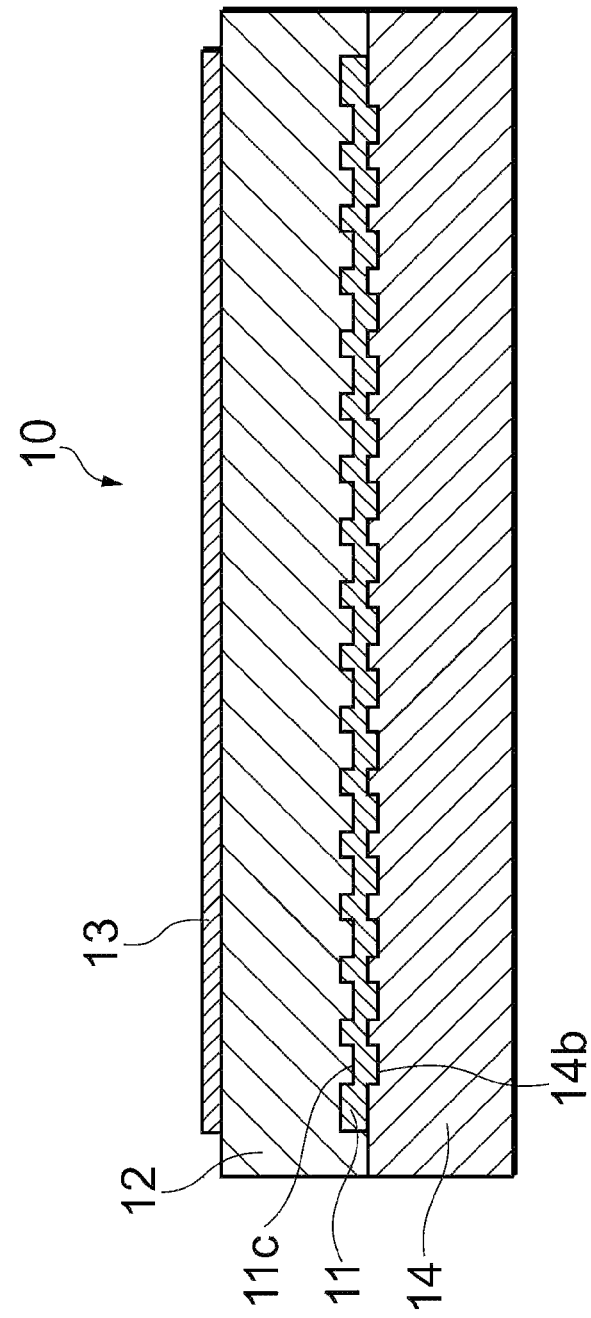
FIG. 13 is a cross-section sectional diagram for explaining an alternate example of the sensor portion shown in FIG. 10 and FIG. 11.

FIG. 12 and FIG. 13 are cross-sectional diagrams for explaining an alternate example of the sensor portion 10 shown in FIG. 10 and FIG. 11. Note that as with FIG. 6, FIG. 12 is a cross-sectional diagram in the direction of the arrow II-II shown in FIG. 4, and, as with FIG. 7, FIG. 13 is a cross-sectional drawing in the direction of the arrow III-III shown in FIG. 4. As shown in FIG. 12 and FIG. 13, a plurality of recessed portions 14b may be provided on the top face of the substrate 14 together with the provision of the plurality of recessed portions 11c on the top face of the first electrode plate 11.

As with the raised portions 14a, the recessed portions 14b may be formed using, for example, a chemical etching method, a dry etching method, a reactive ion etching (RIE) method, or a micro-machining technology (an MEMS technology) such as a laser machining method, or a machining technology such as a sandblasting method, a thin film deposition technology such as epitaxial deposition, or a film depositing technology such as vapor deposition or a sputtering method, or the like.

As illustrated in FIG. 6 and FIG. 7, the humidity-sensitive film 12 is provided on the top face of the first electrode plate 11. Here there is a problem with the humidity-sensitive film swelling and having a reduction (degradation) in sensitivity to humidity in the conventional humidity sensor when disposed in a high-humidity environment or when a specific amount of time (months) has elapsed since use. Moreover, there has been the risk of delamination (peeling) of the humidity-sensitive film from the electrode plate due to the stress due to swelling (expansion) of the humidity-sensitive film. In contrast, in the humidity sensor 100 according to the present example of the surface area of the face of the first electrode plate 11 on the humidity-sensitive film 12 side is increased through the formation of the recessed portions and raised portions on the top face of the first electrode plate 11.

The humidity-sensitive film 12 is structured from, for example, a methyl methacrylate plastic (PMMA), a cross-linked methyl methacrylate plastic, or an organic polymer plastic such as a polyimide, polysulfone, polyether sulfone, or a fluorine-including polyimide. The thickness of the humidity-sensitive film 12 is between, for example, 1 µm and 10 µm.

Moreover, as the method for fabricating the humidity-sensitive film 12, the aforementioned organic polymer plastic may first be coated onto the substrate 14, the first electrode plate 11, and the underlying electrode 15 through a spin coating method, a dipping method, a spray coating method, or the like, and then dried through performing a heat treatment. Following this, the organic polymer plastic on top of the first connecting terminal 11a and the underlying electrode 15 is removed selectively through a vapor-phase reactive ion etching method, a sputtering method, an atmospheric-pressure plasma etching method, or a physical removal method that does not damage the electrode plate, or the like. Doing so forms the humidity-sensitive film 12 and exposes the first connecting terminal 11a and the underlying electrode 15.

The second electrode plate 13 includes a second connecting terminal 13a, and is disposed on top of the humidity-sensitive film 12. The second connecting terminal 13a is formed so as to contact the underlying electrode 15 on the substrate 14.

The second electrode plate 13 is structured from a metal layer such as, for example, platinum (Pt), gold (Au), chrome (Cr), palladium (Pd), or the like. The thickness of the second electrode plate 13 may be, for example, between several hundred nanometers (or several thousand angstroms) and 1 µm.

As the method for forming the second electrode plate 13, for example, first a patterning method through a film deposition method such as a vapor deposition or a sputtering method, a lift-off method, or a metal masking method, or the like, may be used to deposit a metal film onto the humidity-sensitive film 12 and the substrate 14. The deposited metal film is structured having a porous structure, or with a structure having fine cracks. Moreover, patterning is performed to protect over the first connecting terminal 11a, and the like, so that the metal film of the second electrode plate 13 selectively does not adhere thereto. Doing so forms both the second electrode plate 13 and the first connecting terminal 11a.

A first electrode pad 17 is provided on the exposed first connecting terminal 11a, and a second electrode pad 18 is provided on the exposed second connecting terminal 13a. The first electrode pad 17 and the second electrode pad 18 are formed using, for example, patterning or metal masking through, for example, a lift-off method, a vapor deposition method, a sputtering method, or the like. The material for the electrode pad is a metal film having at least one layer of gold (Au), platinum (Pt), aluminum (Al), copper (Cu), gold/niobium (Au/Nb), gold/chrome (Au/Cr), gold/titanium (Au/Ti), platinum/niobium (Pt/Nb), platinum/chrome (Pt/Cr), platinum/titanium (Pt/Ti), platinum/gold/niobium (Pt/Au/Nb), platinum/gold/chrome (Pt/Au/Cr), or platinum/gold/titanium (Pt/Au/Ti), or the like. Moreover, respective lead lines (not shown) are connected to the first electrode pad 17 and the second electrode pad 18. Doing so makes it possible to access (output), as the detection signal, the current that flows between the first electrode plate 11 and the second electrode plate 13.

Figure 14:
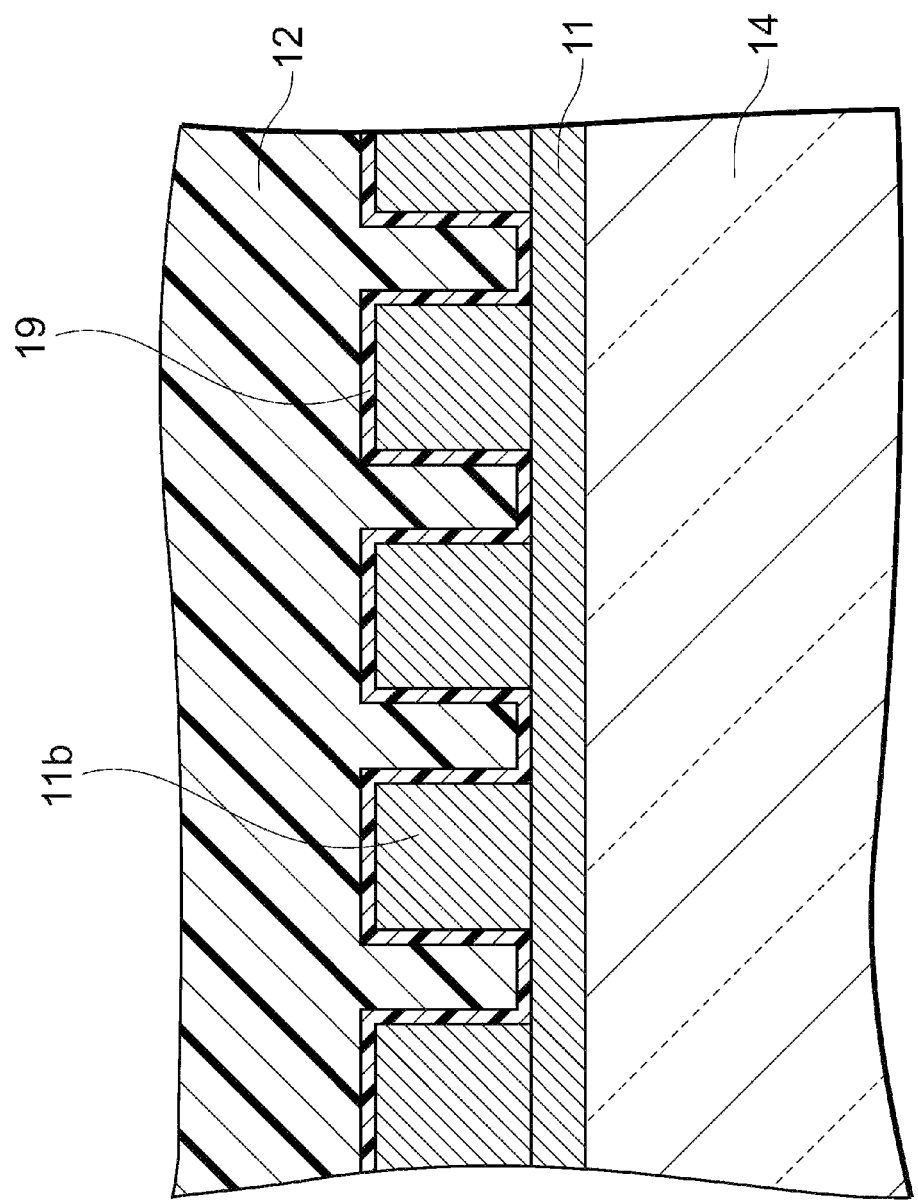
FIG. 14 is an enlarged cross-sectional diagram of critical portions of the sensor portion shown in FIG. 4.

FIG. 14 is an enlarged cross-sectional diagram of critical portions of the sensor portion shown in FIG. 4. As illustrated in FIG. 14, a coupling layer 19 is disposed between the first electrode plate 11 and the humidity-sensitive film 12, and the humidity-sensitive film 12 is adhered to the top surface of the first electrode plate 11.

The coupling layer 19 is structured from, for example, a silane coupling agent having, for example, silanol groups (—SiOH) and amino groups (—NH$_3$).

Moreover, as a method for fabricating the coupling layer 19, for example, a plurality of raised portions 11b may be formed on the top face of the first electrode plate 11, after which the silane coupling agent may be deposited onto the substrate 14, the first electrode plate 11, and the underlying electrode 15 through, for example, a spin coating method, a dipping method, a spray coating method, or the like. The coupling layer 19 is formed thereby. The silanol groups (—SiOH) of the silane coupling agent have a dehydrating condensing reaction with the silanol groups (—SiOH) on the surface of the first electrode plate 11, to form covalent bonds (—Si—O—Si—). Moreover, the amino groups (—NH$_3$) of the silane coupling agent react with the humidity-sensitive film 3. In this way, the provision of the coupling layer 19 for adhering the humidity-sensitive film 12 to the top surface of the first electrode plate 11 increases the adhesion between the first electrode plate 11 and the humidity-sensitive film 12, not only decreasing the likelihood that the humidity-sensitive film 12 can delaminate, but also making it possible to suppress the reduction in sensitivity due to swelling of the humidity-sensitive film 12.

Figure 15:
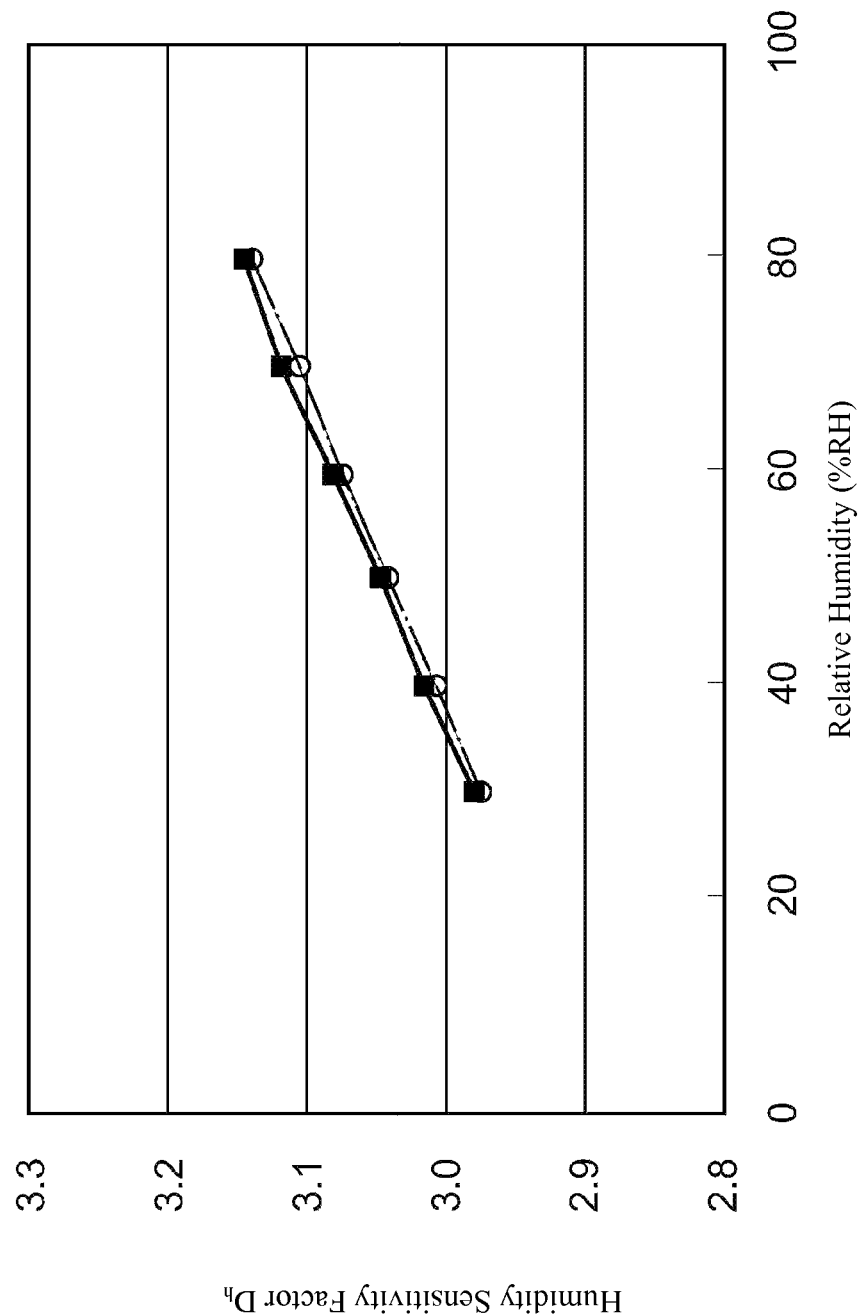
FIG. 15 is a graph showing the relationship between the relative humidity and the humidity sensitivity factor.
Figure 16:
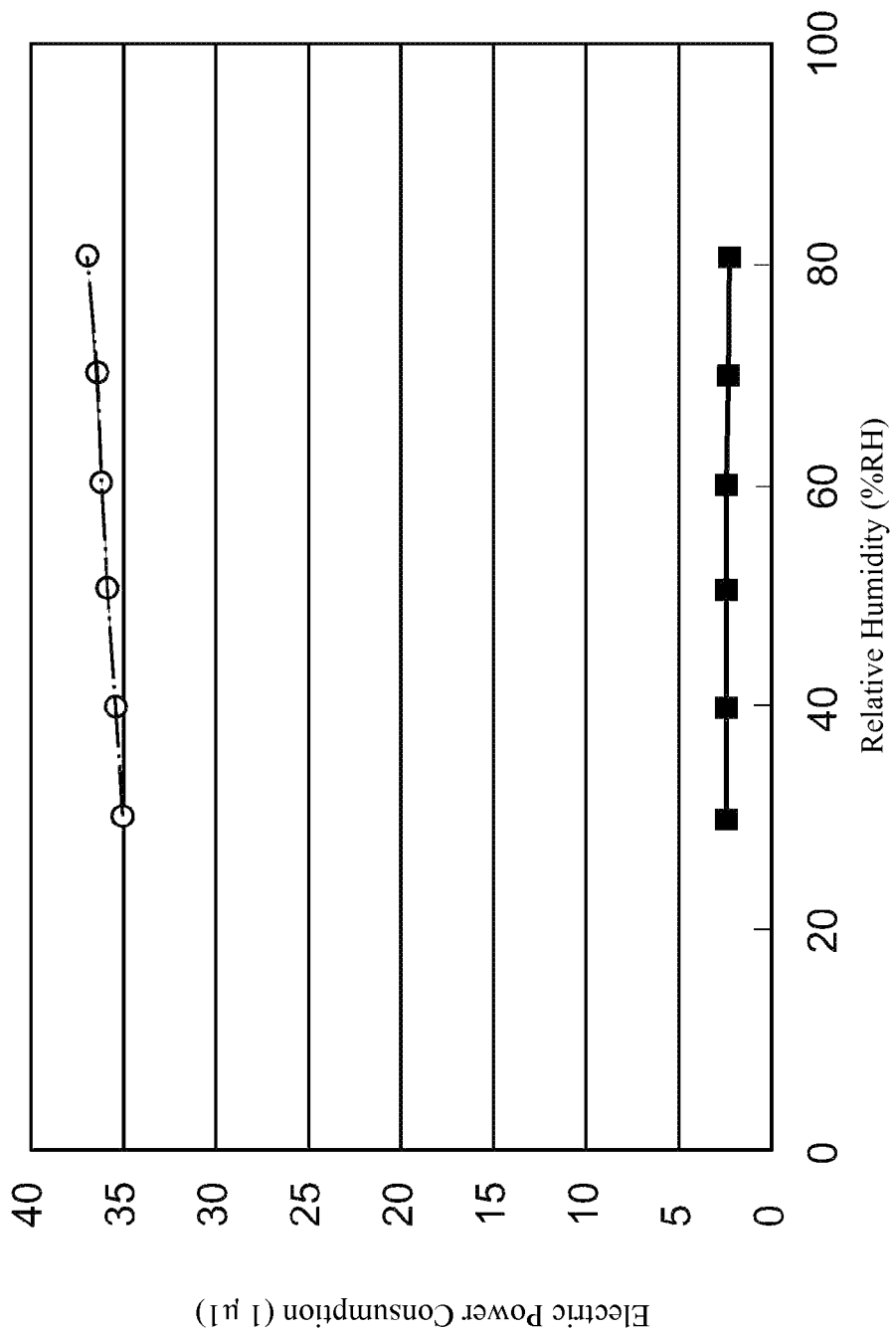
FIG. 16 is a graph showing the relationship between the relative humidity and power consumption.

FIG. 15 is a graph illustrating the relationship between the relative humidity and the humidity sensitivity factor, and FIG. 16 is a graph showing the relationship between the relative humidity and the electrical power consumption. Note that in FIG. 15 and FIG. 16, the solid lines are the humidity sensor 100 in the present example, and the dotted lines show the case of the conventional humidity sensor. Moreover, for ease in the comparison, in the experiments a humidity sensor 100 according to the present example and a conventional humidity sensor were placed in a humidity-controllable high-temperature chamber, where the relative humidity was varied while keeping the temperature constant, and an impedance meter was used to set the AC voltage and frequency to specific (constant) values. Moreover, for ease in the comparison, in the experiments a humidity sensor 100 according to the present example and a conventional humidity sensor were placed in a humidity-controllable high-temperature chamber, where the relative humidity was varied while keeping the temperature constant, and an impedance meter was used to set the AC voltage and frequency to specific (constant) values. As illustrated in FIG. 15, the humidity sensor 100 according to the present example and the conventional humidity sensor can be seen to have similar humidity sensitivity factors Dh for humidity variations between 30% Rh and 80% Rh, and have identical, or essentially identical, humidity sensitivity characteristics. On the other hand, as illustrated in FIG. 16, for variations in humidity between 30% Rh and 80% Rh, the conventional humidity sensor can be seen to have a tendency for the electrical power consumption to increase from about 35 µW to about 38 µW. This can be considered to be because of the increase in the electrostatic capacitance $C_1$ due to the increase in the humidity sensitivity factor of the dielectric film, illustrated in FIG. 15, accompanying the increase in humidity, which increases the electric current that flows between the two electrode plates due to the decrease in the impedance in the sensor portion, as shown in Equation (3), above. In contrast, in the humidity sensor 100 according to the present example, for the variation in the humidity between the relative humidity of 30% Rh to 80% Rh, the electrical power consumption showed increases and decreases in the order of hundreds of nW, centered on about 2 µW. These results indicate that the humidity sensor 100 according to the present example is able to reduce the amount of electrical power consumed to less than about ⅕ of that of the conventional humidity sensor when the relative humidity is in a range between 30% Rh and 80% Rh.

While, in the present example, the explanation was for a humidity sensor for detecting the humidity in the ambient environment being measured, as an environment sensor for detecting a specific physical quantity in the environment, there is no limitation thereto. Instead, it may be an environment sensor for detecting another physical quantity, where the specific physical quantity is, for example, temperature, pressure, radiation temperature, luminosity, airflow, vibration, inclination, position, ambient gas, dust, or the like.

In this way, in the humidity sensor 100 in the present example, the sensor portion 10 to which the AC voltage is applied is structured so as to have higher impedance than in the sensor portion of a conventional humidity sensor. As a result, it is possible to reduce the amount of power consumed in the sensor portion 10 when compared to that of a conventional humidity sensor. Doing so makes it possible to reduce the amount of electrical power consumed in the humidity sensor 100 as a whole in the examples of the present invention, including the sensor portion 10, when compared to that of a conventional humidity sensor. Moreover, the humidity sensor 100 according to the present example may be applied well to not only devices with fixed power supplies, but also devices that are supplied with power from mobile power supplies or batteries, energy harvesting devices (environmental electrical power generators) that generate their own electricity through weak energy such as, for example, solar power electric generation, a temperature differential electric generation, vibrational electric generation, bioelectric generation, airflow or wind-power electric generation, hydropower electric generation, wave power electric generation, rotary electric generation, or the like, and also to devices that are provided with mobile fuel cells, and, in particular, to devices that perform wireless communications that are mobile or portable.

Moreover, in the humidity sensor 100 in the present example, the distance $d_h$ between the first electrode plate 11 and the second electrode plate 13, and the surface areas $S_h$ of the first electrode plate 11 and the second electrode plate 13, are set based on the impedance $Z_h$ of the sensor portion 10. If there is a sensor portion with a distance $d_1$ between the two electrode plates, surface areas $S_1$ of the two electrode plates, a humidity sensitivity factor $D_h$, and an electrostatic capacitance $C_1$ ($=D_h \times S_1/d_1$) in a conventional humidity sensor of an electrostatic capacitance type wherein the electrostatic capacitance varies in accordance with the humidity, then the electrostatic capacitance $C_h$ of the sensor portion can be made smaller than the electrostatic capacitance $C_1$ ($C_h < C_1$), and the impedance $Z_h$ of the sensor portion 10 in the present invention can be made higher than the impedance $Z_1$ of the sensor portion of the conventional humidity sensor ($Z_h > Z_1$) through setting the distance $d_h$ between the two plates in the humidity sensor 100 according to the present example to be larger than the distance $d_1$ ($d_h > d_1$), setting the surface areas $S_h$ in the humidity sensor 100 according to the present example to be smaller than the surface area $S_1$ ($S_h < S_1$), or both. Consequently, it is possible to cause the electrostatic capacitance $C_h$ of the sensor portion 10 according to the present example to be less than that of the electrostatic capacitance $C_1$ of the sensor portion of the conventional humidity sensor through setting the distance $d_h$ and the surface areas $S_h$ based on the impedance $Z_h$ of the sensor portion 10, to make it possible to cause the impedance $Z_h$ of the sensor portion 10 in the present example to be higher than the impedance $Z_1$ of the sensor portion of the conventional humidity sensor. This makes it possible to achieve (structure) the humidity sensor 100 according to the present examples easily.

Moreover, in the humidity sensor 100 according to the present examples, a plurality of recessed portions and raised portions is formed on the surface of the first electrode plate 11 on the humidity-sensitive film 12 side, that is, on the top surface thereof. Here there is a problem with the humidity-sensitive film swelling and having a reduction (degradation) in sensitivity to humidity in the conventional humidity sensor when disposed in a high-humidity environment or when a specific amount of time (months) has elapsed since use. Moreover, there has been the risk of delamination (peeling) of the humidity-sensitive film from the electrode plate due to the stress due to swelling (expansion) of the humidity-sensitive film. In contrast, in the humidity sensor 100 according to the present example the surface area of the face of the first electrode plate 11 on the humidity-sensitive film 12 side is increased through the formation of the recessed portions and raised portions on the top face of the first electrode plate 11. Doing so enables a mitigation of the per-unit-surface-area force that acts on the humidity-sensitive film 12, when compared to the case wherein the recessed and raised portions are not formed on the top face of the first electrode plate, not only reducing the likelihood of delamination of the humidity-sensitive film 12, but also making it possible to suppress the reduction (degradation) of sensitivity caused by the swelling of the humidity-sensitive film 12, thereby enabling stable detection over an extended period of time. Moreover, in particular, this enables an increase in the detection sensitivity of the electrostatic capacitance $C_h$ when the surface area $S_h$ of the first electrode plate 11 has been set so as to be small, based on the impedance $Z_h$ of the sensor portion 10.

Moreover, in the humidity sensor 100 in the present example, a coupling layer 19 for adhering the humidity-sensitive film 12 to the humidity-sensitive film 12 side of the first electrode plate 11, that is, to the top surface thereof, is further provided. This increases the adhesion between the first electrode plate 11 and the humidity-sensitive film 12, thereby not only reducing the likelihood of delamination of the humidity-sensitive film 12, but enabling the suppression of the reduction in sensitivity due to swelling of the humidity-sensitive film 12. This enables stable detection over an extended period of time.

Moreover, in the humidity sensor 100 according to the present example, a substrate 14 for supporting the first electrode plate 11 is also provided. This enables the mechanical strength of the first electrode plate 11 to be reinforced, and is particularly effective in the case wherein the surface area $S_h$ of the first electrode plate 11 is set so as to be small, based on the impedance $Z_h$ of the sensor portion 10.

Moreover, the humidity sensor 140 according to the present examples is further provided with a controlling portion 70 for driving the power supply portion 30 intermittently. Doing so enables a further reduction in the amount of electrical power consumed by the humidity sensor 100, when compared to the case of the sensor portion 10 wherein the power supply portion 30 is driven continuously so that the sensor portion 10 is always supplied power. Moreover, because the electrostatic capacitance $C_h$ in the humidity sensor 100 according to the present example is set, based on the impedance $Z_h$ of the sensor portion 10, to be smaller than the electrostatic capacitance $C_1$ of the conventional humidity sensor (that is, $C_h<C_1$), and thus if the internal resistance $R_{if}$ is the same, the time constant $\tau_h$ of the humidity sensor 100 according to the present example can be smaller than the time constant $\tau_1$ of the conventional humidity sensor (that is, $\tau_h<\tau_1$). As a result, this makes it possible to shorten the time until the steady state is achieved, that is, to shorten the wait time (the stabilization time) until the sensor portion 10 starts up or is stopped, in intermittent driving of the power supply portion 30 by the controlling portion 70. This makes it possible to reduce the amount of electrical power consumed during this waiting time, enabling a further decrease in the amount of electrical power consumed in the humidity sensor 100 according to the present example, when compared to the conventional humidity sensor.

Moreover, the humidity sensor 100 in the present example is provided with an interface circuit portion 50 that includes the power supply portion 30 and that detects the electrostatic capacitance $C_h$ of the sensor portion 10, and a communicating portion 90 for transmitting the electrostatic capacitance $C_h$ that is detected by the interface circuit portion 50. As a result, the electrostatic capacitance $C_h$, which varies in accordance with the ambient humidity, is sent to the outside. This makes it possible to communicate (provide notification) the ambient humidity, detected by the sensor portion 10, to an external device.

Note that the structures in the examples set forth above, may be combined or partially replaced with other structures. Moreover, the structures in the examples of the present invention are not limited to those in the examples set forth above, but rather may be varied in a variety of ways in a scope that does not deviate from the spirit or intent of the present invention.

We claim:

1. An environment sensor comprising:
    a sensor portion detecting a specific physical quantity in an environment, the sensor portion comprising a first electrode plate, a second electrode plate, and a dielectric that is provided between the first electrode plate and the second electrode plate, so that an electrostatic capacitance between the first electrode plate and the second electrode plate changes in accordance with the specific physical quantity; and
    a power supply portion applying an AC voltage between the first electrode plate and the second electrode plate, wherein:
    the sensor portion is structured so as to have an impedance that is higher than that of a sensor portion of a conventional environment sensor; and
    the distance between the first electrode plate and the second electrode plate, and the surface areas of the first electrode plate and the second electrode plate, are set depending on the impedance of the sensor portion.

2. The environment sensor as set forth in claim 1, wherein:
    a plurality of recessed portions and raised portions are formed on a surface of the first electrode plate on the dielectric side.

3. The environment sensor as set forth in claim 1, further comprising:
    a coupling layer adhering the dielectric to the surface of the first electrode plate on the dielectric side.

4. The environment sensor as set forth in claim 1, further comprising:
    a substrate supporting the first electrode plate.

5. The environment sensor as set forth in claim 1, further comprising:
   a controlling portion driving the power supply portion intermittently.

6. The environment sensor as set forth in claim 1, further comprising:
   an interface circuit portion that includes the power supply portion and that detects the electrostatic capacitance; and
   a communicating portion transmitting, to the outside, the electrostatic capacitance detected by the interface circuit portion.

\* \* \* \* \*